United States Patent [19]
Girardot et al.

[11] Patent Number: 5,911,951
[45] Date of Patent: Jun. 15, 1999

[54] METHOD OF STERILIZATION

[75] Inventors: Jean-Marie Girardot; Marie-Nadia Girardot, both of Dunwoody, Ga.

[73] Assignee: Biomedical Design, Inc., Marietta, Ga.

[21] Appl. No.: 09/020,471

[22] Filed: Feb. 9, 1998

Related U.S. Application Data

[60] Provisional application No. 60/037,528, Feb. 10, 1997.
[51] Int. Cl.$^6$ .................. A61L 2/18; A01N 1/00
[52] U.S. Cl. .................. 422/28; 435/1.1
[58] Field of Search .................. 422/1, 28, 40; 435/1.1; 623/2, 11, 66, 901

[56] References Cited

U.S. PATENT DOCUMENTS

| | | | |
|---|---|---|---|
| 4,378,224 | 3/1983 | Nimni et al. | 8/94.11 |
| 4,383,832 | 5/1983 | Fraefel et al. | 8/94.11 |
| 5,104,405 | 4/1992 | Nimni | 623/2 |
| 5,447,536 | 9/1995 | Girardot et al. | 8/94.11 |
| 5,697,972 | 12/1997 | Kim et al. | 623/2 |
| 5,733,339 | 3/1998 | Girardot et al. | 8/94.11 |

FOREIGN PATENT DOCUMENTS

| | | | |
|---|---|---|---|
| 0267434 | 10/1986 | European Pat. Off. | 88/31 |

OTHER PUBLICATIONS

Lee et al. "Crosslinking of tissue–derived biomaterials in 1–ethyl–3–(3–dimethylaminopropyl)carbodiimide (EDC)", J. Mater. Sci.: Mater. Med., pp. 531–541, 1996.

*Primary Examiner*—E. Leigh McKane
*Attorney, Agent, or Firm*—Fitch, Even, Tabin & Flannery

[57] ABSTRACT

Heart valves or other components for replacement of heart or other bodily organs and tissue prostheses or synthetic prosthetic materials are effectively sterilized by treatment with a coupling agent known to create amide linkages between amines and carboxylic acids in the presence of a lower alkanol. Such treatment has been shown to be bactericidal when carried out at 40° C. for over 1 hour. The sterilization treatment preferably employs EDC as a water-soluble coupling agent plus an optional coupling enhancer such as sulfo-NHS or NHS, in the presence of isopropanol or an equivalent alkanol. Such sterilization treatment is preferably carried out at a temperature above ambient temperature in a buffered aqueous solution. The treatment leaves no residuals other than ones which are nontoxic and biocompatible, does not affect the resistance of the tissue to thermal denaturation and to digestion by proteolytic enzymes, and surprisingly also increases the resistance of fixed biological tissue to calcification.

19 Claims, No Drawings

METHOD OF STERILIZATION

This application claims priority from U.S. Provisional Application Serial No. 60/037,528, filed Feb. 10, 1997. The disclosure of this application is incorporated herein by reference.

FIELD OF THE INVENTION

This invention relates to methods of sterilization and more specifically to methods of sterilization which are particularly suited for biological materials, such as organ replacements, and which methods exhibit efficacy against difficult-to-kill bacteria and bacterial spores.

BACKGROUND OF THE INVENTION

Sterilization techniques are widely used and important in industries such as food processing and health care. Saturated steam at temperatures above 110° C. has frequently been used to destroy microorganisms, such as microbial spores. Certain articles, particularly those used for health care, cannot withstand the temperatures and moisture of steam sterilization, and oftentimes such articles are also considered not to be suitable for sterilization by ionizing radiation. As a result, gaseous sterilants have been developed which function at relatively low temperatures and thus offer an attractive alternative. One of the most commonly used gaseous sterilants is ethylene oxide, which is used for medical product sterilization and for other sterilization processes. However, in certain instances, the presence of residual ethylene oxide is considered to be detrimental, even in small quantities, and accordingly improved methods of sterilization, particularly for sterilization of medical products, have continued to be sought.

SUMMARY OF THE INVENTION

It has now been found that sterilization of items, including biological tissue, replacement organs and synthetic prosthetic materials, including polymers and metals, can be effectively carried out by treatment with a coupling agent known to create amide linkages between amines and carboxylic acids which has been proven to be bactericidal. The sterilization treatment may employ an optional coupling enhancer and is preferably carried out at a temperature above ambient in a buffered solution that contains isopropyl alcohol or an equivalent alcohol in an amount effective to achieve penetration of said coupling agent into the cells of the microorganisms. The residuals from such treatment are nontoxic, biocompatible, and water-soluble, so that they can easily be washed off the tissue before implantation in a human body. It was surprisingly found that biological tissue which is sterilized in this manner exhibits enhanced resistance to calcification following implantation within a living body.

DETAILED DESCRIPTION OF THE PREFERRED EMBODIMENTS

The term "coupling agent" is herein used to refer to a chemical reagent that facilitates the formation of amide bonds. Such bonds may be formed between reactive amines and reactive carboxyls on enzymes and proteins as well as with the reactive carboxyl or amine moieties located on and within bioprosthetic tissue. Those having skill in peptide synthesis and related arts will be familiar with such reagents, e.g. water-soluble carbodiimides and succinimides. When this coupling is carried out in the presence of a $C_2$ to $C_4$ alkanol, or other equivalent alcohol, sterilization occurs, destroying bacteria and spores.

The coupling agent and the optional coupling enhancer are preferably water-soluble so the treatment can be effected in aqueous solution, particularly when biological tissue materials are being sterilized. The preferred coupling agent is 1-ethyl-3(3-dimethyl aminopropyl)carbodiimide hydrochloride (EDC); alternative suitable coupling agents include N-hydroxysuccinimide and other water-soluble carbodiimides. When biological tissue is being treated, a water-soluble coupling agent is preferably used. When EDC is used as the coupling agent, the preferred enhancer is N-hydroxysulfosuccinimide (sulfo-NHS), although other suitable enhancers, such as N-hydroxysuccinimide (NHS), can alternatively be used. The concentrations of the coupling agent and of the enhancer (when employed) can be varied somewhat; however, appropriate concentrations are readily determinable by those of skill in the art. Although lower concentrations are effective if the concern is only with certain categories of bacteria, the coupling agent is preferably used in a concentration between about 5 millimolar (mM) and about 100 mM, more preferably between about 15 mM and about 50 mM, and most preferably at between about 20 mM and about 40 mM, in order to be certain of destroying all commonly encountered bacteria and spores. The optional enhancer is preferably employed at a concentration between 0.5 mM and about 30 mM, and more preferably at about 1 mM to about 5 mM.

All solutions used are preferably filtered through 0.45 μm or smaller filters before use. The solution preferably contains at least about 10 volume % and more preferably contains between about 10 and about 30 volume % of a $C_2$ to $C_4$ alkanol or an equivalent alcohol; by volume % is meant volume of alcohol relative to volume of solution. Other alcohols which might be employed include ethanol, propanol, 1-butanol, 2-butanol, tert-butyl alcohol, 1-pentanol, 2-pentanol and tert-pentyl alcohol. A lower alkanol is generally used in an amount which effectively assists the coupling agent in penetrating the cell walls of the bacteria, spores or other microorganisms. Preferably, isopropanol is used in an amount equal to at least about 10 g per 100 ml of solution; more preferably, the solution contains between about 15% and about 25% of isopropanol and most preferably contains about 20 volume % of isopropanol. Of course, higher alcohol concentrations may be used so long as compatible with the material to be sterilized and may reduce the duration of treatment needed. The treatment not only effects sterilization without risk of damage to biological tissue but also may make some contribution to fixation of certain tissue to be implanted; surprisingly, the treatment enhances the resistance of biological tissue to undergo calcification within a living body.

Reaction conditions for the sterilization may vary somewhat depending on the specific coupling agent employed. In general, the sterilization treatment is carried out in an aqueous buffer solution selected from among those that are well known to those of ordinary skill in this art. Examples of suitable buffers include, but are not limited to, N-2-hydroxyethylpiperazine-N'-ethanesulfonic acid (HEPES) and 3-(N-morpholino)propanesulfonic acid (MOPS), and the like.

The pH and concentration of the buffered solution also may vary, again depending upon the coupling agent employed. Preferably, the buffer concentration and pH are chosen to provide an effective sterilization environment while being the least harmful to bioprosthetic material or the like. For example, with EDC as the coupling agent, with or without sulfo-NHS or NHS as an enhancer, the pH of the solution employed is about 6.0 to about 7.0. The temperature of the sterilizing solution may be maintained between about 25° C. and 55° C., although higher temperatures may be used so long as compatible with the materials being sterilized. Preferably, the sterilization is carried out between 35° C. and 45° C. for at least about 1 hour, preferably for at least about 5 hours and more preferably for at least about 12 hours. For polymeric or metallic materials, temperatures higher than 55° C. may be used so long as not harmful to the material being sterilized and may shorten duration of treatment.

Although the sterilization treatment method is considered useful for a wide variety of prosthetic and bioprosthetic materials, it is considered to be particularly useful for sterilizing replacement organ components, such as heart valves, which have been made from animal tissue that has been suitably fixed. It may be desirable to rinse such material first with cold saline prior to sterilization. Inasmuch as sterilization is usually a final step, tissue fixation is normally first carried out. Although glutaraldehyde or other fixation techniques, e.g. polyepoxide crosslinking or photooxidation may be carried out, a fixation process of the types detailed in U.S. Pat. No. 5,447,536 (Sep. 5, 1995) and in U.S. Ser. No. 08/693,076, filed Sep. 24, 1996, the disclosures of which are incorporated herein by reference, is preferably used.

The material being sterilized is usually maintained in contact with the sterilization solution for about 5 to 72 hours, and it is found that such treatment effectively inactivates even hard-to-kill bacteria and spores, thus proving to be potently bactericidal. Moreover, this sterilization treatment does not adversely affect bioprosthetic tissue, as by possibly lowering the shrinkage temperature of such sterilized material or by lowering its resistance to proteolytic degradation by collagenase or by proteases, and has surprisingly been found to increase resistance to calcification.

The present invention is further described by the examples that follow. These examples are not to be construed as limiting in any way either the spirit or the scope of the present invention.

Devices to be implanted in the human body are required to be sterilized in a manner to effectively destroy all microorganisms. Due to the unique applications of liquid chemicals for use in sterilization processes, it is necessary to be vigilant in detecting, screening and testing microorganisms which could pose significant resistance to the sterilization process. Examples of reference microorganisms which have previously demonstrated high resistance to liquid chemical sterilants are: the spores of *Bacillus subtilis, Clostridium sporogenes, Bacillus pumilus, Chaetonium globosom* and *Microascus cinereus* and representative vegetative cells, such as *Mycobacterium chelonae, Methylbactrium extorquens,* and *Trichosporon aquatile.* Of the foregoing, the most resistant may be the spores of *Bacillus subtilis.* The coupling agent used in the following examples is 1-ethyl-3 (3-dimethyl aminopropyl) carbodiimide hydrochloride (EDC), and when used, the optional enhancer is either N-hydroxy-sulfosuccinimide (sulfo-NHS) or hydroxysuccinimide (NHS), which are all commercially available. Peptone water was prepared by dissolving 1 g of Bacto Peptone in 1 liter of de-ionized water. The solution was then filtered into sterile bottles using sterile 0.2 micron filters. All agents are solubilized in 10 mM HEPES buffer containing 0.85% of sodium chloride, pH 6.5 (HEPES buffer). Concentrations are expressed as mM (number of millimoles of chemical for each liter of solution), or as % (grams per 100 ml of solution). Temperatures are in ° C. (degrees Celsius), with room temperature being about 20–25°.

Porcine aortic roots are fixed by cross-linking according to the method described in U.S. Pat. No. 5,447,536. After fixation, the valves are stored in 10 mM HEPES, 0.85% NaCl, 20% isopropyl alcohol, pH 7.4, at 4° C. The sterility tests described in the following examples were in most cases conducted in the presence of bioprosthetic heart valve tissue, but when such tissue was not present, the solutions were filtered through a 0.45 micron filter attached to a funnel (filter funnel). The filters were then rinsed with peptone water to eliminate residual chemicals on the membrane that may prevent growth of the organisms tested. The membrane filters were then incubated on TSA plates at about 32° to 33° C., e.g. 32.5° C. When an aortic valve was inoculated with microorganisms for test purposes and then submitted to sterilization, the solution was filtered as described above. The aortic valve tissue was then washed for 20 minutes in a reciprocating shaker in the presence of peptone water containing Tween 80 in order to extract all indigenous spores or microorganisms from the tissue. This solution was filtered and then incubated as described above. All microbiological testing is performed in a biological laminar flow hood to prevent contamination. The shrinkage temperature and the proteolytic (collagenase and protease) degradation tests are conducted as previously described in the '536 patent. Resistance to calcification is assessed by subdermal implantation of sterilized leaflets and aortic wall coupons in young rats, as also described in the '536 U.S. patent.

EXAMPLE 1

*Mycobacterium chelonae* ATCC 35752 ($\sim 10^5$) was inoculated in sterile cups. A 10 mM HEPES, 0.85% NaCl, pH 6.5 solution containing 10 mM EDC and 1 mM Sulfo-NHS in the presence or absence of 20% isopropyl alcohol was maintained in contact with the bacteria in the cups for various periods of time (treatment duration). The cups were maintained at room temperature, and the solutions were then filtered. The filters were then incubated at about 32–33° C. for up to 6 weeks (incubation duration) using either Trypticase Soy Agar (TSA) plates or Trypticase Soy Broth (TSB). All inoculations were done in duplicate.

RESULTS

| Treatment Duration | Incubation Duration | | | | |
|---|---|---|---|---|---|
| | 1 Day | 1 Week | 3 Week | 4 Week | 6 Week |
| NO ISOPROPYL ALCOHOL | | | | | |
| 0 hour | +,+ | +,+ | +,+ | +,+ | +,+ |
| 12 hours | +,+ | +,+ | +,+ | +,+ | +,+ |
| 24 hours | −,− | +,+ | +,+ | +,+ | +,+ |
| 48 hours | −,− | −,− | −,− | −,+ | −,+ |
| 72 hours | −,− | −,− | −,− | −,− | −,+ |
| | TSA,TSB | TSA,TSB | TSA,TSB | TSA,TSB | TSA,TSB |
| 20% ISOPROPYL ALCOHOL | | | | | |
| 0 hour | −,− | −,− | +,+ | +,+ | +,+ |
| 12 hours | −,− | −,− | −,− | −,− | −,− |
| 24 hours | −,− | −,− | −,− | −,− | −,− |
| 48 hours | −,− | −,− | −,− | −,− | −,− |
| 72 hours | −,− | −,− | −,− | −,− | −,− |
| | TSA,TSB | TSA,TSB | TSA,TSB | TSA,TSB | TSA,TSB |

(+) Indidates growth while (−) indicates no growth or complete kill.

The results indicate that, in the presence of 20% sopropyl alcohol, room temperature treatment with EDC plus sulfo-NHS kills all *Mycobacterium chelonae* within 12 hours of sterilization treatment.

EXAMPLE 2

A sterilization process similar to Example 1 is carried out using *Bacillus subtilis* spores ($\sim 10^6$) inoculated in sterile cups some of which contain cross-linked heart valves that had been fixed by a process according to U.S. Pat. No. 5,447,536. A 10 mM HEPES, 0.85% NaCl, pH 6.5 solution containing 20 mM EDC and 1 mM Sulfo-NHS in the presence of 20% isopropyl alcohol was added for various periods of time (treatment duration). The cups and the heart valves were maintained at 40° C. for the term of the treatment. The solutions were then filtered and the filters incubated for up to 7 days (incubation duration) at about 32–33° C. using Trypticase Soy Agar (TSA) plates. All inoculations were done in duplicate.

RESULTS

| Treatment Duration | Incubation 1 Day | Duration 7 Days |
|---|---|---|
| WITHOUT VALVES | | |
| 24 hours | − | − |
| 48 hours | − | − |
| 72 hours | − | − |
| WITH VALVES | | |
| 48 hours | − | − |
| 72 hours | − | − |

(+) indicates growth, while (−) indicates no growth or complete kill.

The results demonstrate that the spores of Bacillus subtilis are inactivated with this method of sterilization in the absence or presence of porcine aortic valve tissue.

EXAMPLE 3

In the experiments described above, a coupling enhancer (Sulfo-NHS) was added to EDC during the sterilization process. The following experiment was designed to test the efficacy of EDC in the presence or absence of an enhancer. A sterilization test process was carried out employing about 5.7 to $6.6 \times 10^5$ Bacillus subtilis ATCC 9372 spores, inoculating them in sterile cups for 10 minutes. A solution of 10 mM HEPES, 0.85% NaCl, 20% isopropyl alcohol, pH 6.5 was then added to each of the cups, which solution contains 20 mM EDC and either 1 mM Sulfo-NHS or 1 mM NHS or no enhancer. Incubation was carried out for 72 hours (treatment duration) with the cups at about 40° C., and the solutions from the cups were then filtered. The filters were rinsed with a 0.1% peptone water solution to eliminate any residual EDC and/or enhancer and were then incubated on Trypticase Soy Agar (TSA) plates. All inoculations were done in duplicate, and the results are set forth in Table A.

TABLE A

| | | NUMBER OF COLONY FORMING UNITS (SURVIVORS) | | |
|---|---|---|---|---|
| | | | ENHANCER | |
| CONDITIONS | SAMPLES | sulfo-NHS | NHS | NONE |
| CONTROLS | | | | |
| negative | 1 | 0 | 0 | 0 |
| | 2 | 0 | 0 | 0 |
| positive | | | | |
| | 1 | $5.7 \times 10^5$ | $6.1 \times 10^5$ | $6.6 \times 10^5$ |
| | 2 | $5.7 \times 10^5$ | $6.5 \times 10^5$ | $\sim 6.0 \times 10^5$ |

TABLE A-continued

| | | NUMBER OF COLONY FORMING UNITS (SURVIVORS) | | |
|---|---|---|---|---|
| | | | ENHANCER | |
| CONDITIONS | SAMPLES | sulfo-NHS | NHS | NONE |
| TESTS | | | | |
| | 1 | 0 | 0 | 0 |
| | 2 | 0 | 0 | 0 |

The results demonstrate that EDC and isopropanol, either in the presence or absence of enhancer such as sulfo-NHS or NHS, is a potent bactericide against the spores of Bacillus subtilis.

EXAMPLE 4

The following experiment was designed to test the effect of EDC concentration, of temperature and of duration of incubation on the inactivation of spores of Bacillus subtilis. The EDC concentrations tested were 5, 12.5 and 20 mM; the temperatures were 25, 32.5 and 40° C. for 4, 24 and 44 hours of incubation. The tests were carried out under the conditions as set forth in Table B. Spores of Bacillus subtilis (about $2.5 \times 10^5$ per sample) were inoculated on tissue that had been cross-linked using the fixation method described in the '536 patent. The spores were allowed to contact the tissue for 10 minutes, after which time 50 ml of a solution of EDC at the concentration indicated above were added to each cup containing the tissue plus the spores, and incubation was carried out at their respective temperatures and for the respective lengths of time. After such incubation for either 4, 24 or 44 hours, the solutions were filtered to recover the spores, and these were incubated on TSA plates for 2 weeks at 32 to 33° C. The tissue samples were washed with a solution containing a surfactant to fully extract the spores from the tissue, and the resulting solutions were filtered. After washing with 0.1% peptone water, the filters were incubated on TSA plates for 2 weeks at 32 to 33° C. in order to determine the number of survivors on or in the tissue. The colonies were enumerated for both the EDC solutions and the tissue wash solutions, and the results (numbers of colony forming units) were added. The positive and negative controls were shown to be valid for the test. The results are presented in Table B.

TABLE B

| CONDI-TION | EDC (mM) | TEMP. °C. | TIME (hrs) | SURVIVORS # CFUs | LOG REDUCTION |
|---|---|---|---|---|---|
| 1 | 5 | 25 | 4 | 135000 | .27 |
| 2 | 5 | 25 | 44 | 1300 | 2.3 |
| 3 | 5 | 32.5 | 24 | 208 | 3.0 |
| 4 | 5 | 40 | 4 | 1100 | 2.4 |
| 5 | 5 | 40 | 44 | 21 | 4.1 |
| 6 | 12.5 | 25 | 24 | 225 | 3.0 |
| 7 | 12.5 | 32.5 | 4 | 5900 | 1.6 |
| 8 | 12.5 | 32.5 | 24 | 57 | 3.6 |
| 9 | 12.5 | 32.5 | 24 | 34 | 3.9 |
| 10 | 12.5 | 32.5 | 24 | 94 | 3.4 |
| 11 | 12.5 | 32.5 | 24 | 44 | 3.7 |
| 12 | 12.5 | 32.5 | 44 | 33 | 3.9 |
| 13 | 12.5 | 40 | 24 | 27 | 4.0 |
| 14 | 20 | 25 | 4 | 31400 | 0.9 |
| 15 | 20 | 25 | 44 | 16 | 4.2 |
| 16 | 20 | 32.5 | 24 | 24 | 4.0 |

TABLE B-continued

| CONDITION | EDC (mM) | TEMP. °C. | TIME (hrs) | SURVIVORS # CFUs | LOG REDUCTION |
|---|---|---|---|---|---|
| 17 | 20 | 40 | 4 | 5 | 4.7 |
| 18 | 20 | 40 | 44 | 0 | 5.4 |

The results demonstrate that the bactericidal activity of EDC is dependent on the concentration of EDC, the temperature of incubation and the duration of incubation. In additions it can be seen that EDC at 20 mM concentration kills all the spores on cross-linked tissue between 4 and 44 hours at 40° C. A logarithmic reduction of about 4.7 was obtained after 4 hours of incubation at 40° C., and no survivors were present after 44 hours of incubation. In additions a logarithmic reduction of about 4 was achieved at 40° C. after 44 hours of incubation in the presence of only 5 mM EDC, indicating that EDC is a potent bactericidal agent.

EXAMPLE 5

An experiment was designed to test the bactericidal activity of the EDC treatment using two sequential inoculations of at least $1 \times 10^6$ spores of Bacillus subtilis per sample. In the first step, $1.43 \times 10^6$ spores ($Log_{10}$=6.2) were inoculated in triplicate for 10 minutes onto 45 porcine valves which had been cross-linked using a method as described in the above-mentioned patent and patent application. Solutions of 25 mN EDC in 10 mM HEPES, 0.85% NaCl, 20% isopropyl alcohol, at pH 6.5 were poured into the cups containing the valve samples. After 2, 4, 6, and 8 hours of incubation at 40° C., the total surviving spores from 12 samples (solution plus tissue) were counted. After 8 hours of incubation, an additional $1.2 \times 10^6$ ($Log_{10}$=6.1) spores were added to the remaining 33 samples. Summarizing, these remaining 33 samples were thus inoculated at t=0 with $1.43 \times 10^6$ spores and at t=8 with $1.2 \times 10^6$ spores. After various durations of incubation (see Table C for details), the surviving spores in solution and on the valve tissue were removed by filtering and incubated on TSA plates as described above. The positive and negative controls were determined to be valid for the test.

The results are presented in Table C which follows. The results demonstrate that a 6.2 log reduction (no survivors) of Bacillus subtilis spores is achieved within 6 hours of incubation with EDC in the presence of isopropanol and that another 6.1 log reduction is achieved within 6 hours after rechallenge. Complete sterilization of the tissue valve samples and the solution was achieved in this manner.

TABLE C

| Incubation | Mean of Three Samples | | |
|---|---|---|---|
| Duration Hours @ 40° C. | Total Survivors # CFUs | Total Survivors Log 10 | LOG Reduction |
| 0 | $1.43 \times 10^6$ | 6.2 | 0 |
| 2 | 58 | 1.7 | 4.5 |
| 4 | 4 | 0.5 | 5.6 |
| 6 | 0 | 0 | 6.2 |
| 8 | 0 | 0 | 6.2 |
| 8 Rechallenge | $1.2 \times 10^6$ | 6.1 | n/a |
| 11 | 300 | 2.5 | 3.7 |
| 14 | 0 | 0 | 6.1 |

TABLE C-continued

| Incubation | Mean of Three Samples | | |
|---|---|---|---|
| Duration Hours @ 40° C. | Total Survivors # CFUs | Total Survivors Log 10 | LOG Reduction |
| 20 | 0 | 0 | 6.1 |
| 24 | 0 | 0 | 6.1 |
| 28 to 56 | 0 | 0 | 6.1 |

EXAMPLE 6

The foregoing experiments have generally shown that the sterilization effect of EDC plus a lower alkanol could be equally demonstrated by testing biological tissue which had been inoculated with bacteria or by simply testing similar amounts of bacteria which have been inoculated into sterile cups. In view of the foregoing verification, it was decided to test the effectiveness of the sterilization process against other bacteria using sterile cups. Added to each of the cups is 20 ml of 10 mM HEPES, 0.85% NaCl, 20% isopropanol, pH 6.5, containing 25 mM EDC without any coupling enhancer, before the cups are placed in an incubator at 40° C. When the solution temperature reached about 38° C., approximately $10^5$–$10^6$ organisms were inoculated into the solution. The tests were carried out in triplicate. The following four isolates were tested in the form of sporous suspensions. Clostridium sporogenes ATCC 3584, Bacillus pumilus ATCC 27142, Chaetonium globosom ATCC 6205, and Microascus cinereus ATCC 16594. The following three isolates were tested as vegetative cells. Mycobacterium chelonae ATCC 35752, Methylbacterium extorquens ATCC 43645 and Trichosporon aquatile ATCC 22310. The inoculated systems were allowed to incubate for 1 hour, for 5 hours or for 24 hours, and the solutions were then filtered through a 0.45 micron filter. After rinsing, the filter was placed on a TSA plate as described in Example 1. Negative and positive controls indicate that the tests were valid. The results are set forth in Table D which follows wherein the number of CFUs in the inoculum is expressed as its log to the base 10, e.g. $3.4 \times 10^5$=5.5:

TABLE D

| | INOCULUM | Log REDUCTION | | |
|---|---|---|---|---|
| ORGANISM | Log 10 | 1 Hour | 5 Hours | 24 Hours |
| SPORES | | | | |
| Clostridium sporogenes | 4.6 | 2.12 | 3.02 | — |
| | 3.65 | — | — | 3.65 |
| Bacillus pumilus | 5.45 | 3.68 | 4.41 | 5.22 |
| | 5.22 | — | — | — |
| Chaetonium globosum | ~4.7 | — | (72 hrs.)* | (96 hrs.)* |
| VEGETATIVE CELLS | | | | |
| Methylobacterium extorquens | 6.94 | 6.94 | 6.94 | — |
| Trichosporon aquatile | 4.3 | 4.3 | 4.3 | — |
| Mycobacterium chelonae | 5.15 | 5.15 | — | — |

*no growth was observed after stated hours of incubation of plates.

The results indicate that, after one hour of incubation, all vegetative cells had been effectively inactivated. The more resistant spores of certain bacteria were inactivated in a time-dependent manner within 24 hours of incubation with sterilant. The tests show that, against forms of representative bacteria, EDC in the presence of isopropanol is a very good sterilant showing time-dependent inactivation of spores at about 38° C.

EXAMPLE 7

To determine any potentially adverse effect this sterilization may have on shrinkage temperature of the tissue, porcine aortic valves, which had been cross-linked using the method described above in the pending '076 patent application by treatment with EDC in the presence of either sulfo-NHS or NHS as a coupling enhancer, were sterilized using 25 mM EDC in 10 mM HEPES, 0.85% NaCl, 20% isopropyl alcohol, pH 6.5, at 40° C. for 24 hours. This duration of incubation has been shown in Table C to twice achieve a logarithmetic reduction of spores of *Bacillus subtilis* of about 6 in the sequential testing. The leaflets were dissected and the thermal denaturation temperature was determined for each as described in the '536 patent. The results are presented in Table E and demonstrate that this sterilization method has no adverse effect on the shrinkage temperature of the tissue regardless of which fixation process had been used.

TABLE E

| | DENATURATION TEMPERATURE (°C.) | | | |
|---|---|---|---|---|
| SAMPLES | NHS | NHS STERILIZED | sulfo-NHS | sulfo-NHS STERILIZED |
| LEAFLETS | 85.6 ± 0.2 | 85.0 ± 0.2 | 87.5 ± 0.3 | 87.0 ± 0.2 |

It can be seen from Table E that the shrinkage temperature does not change after sterilization.

To determine any effect this sterilization may have on susceptibility of the tissue to proteolytic degradation, porcine aortic valves similarly cross-linked using the method described in the pending patent application in the presence of either sulfo-NHS or NHS as a coupling enhancer were sterilized, using 25 mM EDC in 10 mM HEPES, 0.85% NaCl, 20% isopropyl alcohol, pH 6.5, at 40° C. for 24 hours. Aortic valve leaflets and aortic wall coupons were dissected, and they were then submitted to standard collagenase and protease degradation testing. Such testing is described in detail in the previously mentioned patent and patent application. The results of collagenase digestion testing are expressed as nanomoles of amine released per mg of dry tissue and are presented in Table F.

TABLE F

| | AMINES RELEASED (nmol/mg dry tissue) | | | |
|---|---|---|---|---|
| SAMPLES | NHS | NHS STERILIZED | sulfo-NHS | sulfo-NHS STERILIZED |
| LEAFLETS | 12.0 ± 0.3 | 12.4 ± 1.2 | 14.5 ± 1.5 | 14.9 ± 1.3 |
| AORTIC WALL | 12.3 ± 0.6 | 10.9 ± 0.5 | 13.1 ± 0.8 | 10.0 ± 0.5 |

The results are presented as means ±SEM of six samples. There is no significant difference for the leaflets before and after sterilization, p=0.718 and p=0.994 for NHS and sulfo-NHS respectively. For the aortic wall coupons, there is a significant difference which indicates that they exhibit greater resistance to collagenase after sterilization, i.e., p=0.046 and p=0.0099 for NHS and sulfo-NHS, respectively. Thus, not only is the resistance to collagenase digestion not adversely affected by this EDC sterilization, in some instances, it may be improved. For comparison, previous experiments conducted under similar conditions showed that the level of amines released from fresh tissue were approximately 2150 and 430 nanomoles/mg of tissue for leaflets and aortic wall coupons, respectively.

The results of protease digestion testing are presented in Table G; results for glutaraldehyde-fixed tissue are also shown for comparison purposes. They indicate that there is no significant difference as a result of this sterilization of tissue cross-linked according to the method described in the '076 patent application when either NHS or sulfo-NHS is used as a coupling enhancer; the results obtained following the use of EDC for sterilization for either leaflets on aortic wall coupons show no adverse effect and a resistance equal to that of glutaraldehyde fixation.

TABLE G

| | % ORIGINAL WEIGHT DIGESTED | | | | |
|---|---|---|---|---|---|
| SAMPLES | GLUTAR-ALDE HYDE-FIXED | NHS | NHS STERILIZED | sulfo-NHS | sulfo-NHS STERILIZED |
| LEAFLETS | 31.6 ± 5.7 | 28.1 ± 1.7 | 32.3 ± 1.3 | 29.5 ± 2.6 | 31.9 ± 2.2 |
| AORTIC WALL | 74.5 ± 1.2 | 73.8 ± 1.0 | 75.1 ± 0.9 | 75.1 ± 0.9 | 75.6 ± 2.2 |

To determine the effect this sterilization may have on resistance to calcification, samples of (a) glutaraldehyde-fixed porcine aortic valve leaflets and of (b) porcine aortic valve leaflets cross-linked according to the method of the '076 patent application, which were sterilized using EDC in the presence of isopropanol as described above for the shrinkage temperature experiment, were implanted subdermally in young rats for four weeks. The samples were then retrieved, and quantitative calcium analysis was conducted using Atomic Absorption Spectrophotometry. The results are presented as means ±SEM of six samples per condition in the following Table H.

TABLE H

| | CALCIUM (mg/g dry sample) | | | | |
|---|---|---|---|---|---|
| SAMPLES | Glutaraldehyde-fixed (n = 4) | NHS before ster. (n = 6) | NHS after ster. (n = 6) | sulfo-NHS before ster. (n = 6) | sulfo-NHS after ster. (n = 6) |
| LEAFLETS | 195 ± 8.9 | 23.7 ± 11.4 | 2.9 ± 1.4 | 25.2 ± 10.9 | 0.9 ± 0.1 |
| AORTIC WALL | 66.8 ± 4.5 | 53.2 ± 4.7 | 35.4 ± 6.1 | 54.2 ± 1.5 | 43.6 ± 3.5 |

The results demonstrate that the sterilization method using EDC at 25 mM in the presence of 20% isopropyl alcohol at 40° C. has no adverse effect on the resistance of the porcine aortic valve tissue to calcification. Moreover, it surprisingly shows that the sterilized samples are more resistant to calcification than the samples that were not sterilized. In addition, all the samples cross-linked according to the above-identified patent application are significantly less calcified than samples that had been cross-linked according to the standard glutaraldehyde method.

The results indicate that a solution of EDC in the presence of 20% isopropyl alcohol at about 40° C., with or without NHS or sulfo-NHS, is a powerful bactericide against spores of *Bacillus subtilis* and other bacteria. Vegetative cells of *Mycobacterium chelonae* were effectively inactivated at room temperature by EDC+Sulfo-NHS in the presence of 20% isopropyl alcohol, and subsequent tests with a variety of other vegetative cells showed that 25 mM EDC in 20% isopropanol is an effective sterilant for biological tissue. It is believed that treatment with a coupling agent in the presence of isopropyl alcohol or an equivalent alkanol and at slightly elevated temperature, and optionally with a coupling enhancer, has a potent bactericidal effect and is excellently suited for treatment of tissue valves, and is also considered suitable for sterilizing polymers, metals and the like. In addition, not only are the denaturation temperature and the resistance to proteolytic degradation of tissue valves not adversely affected by such sterilization treatment of 12 hours or more, but surprisingly, samples which have been sterilized using this process appear to be significantly more resistant to calcification, the leading cause of tissue valve failure. Compared to tissue fixed by the standard glutaraldehyde method, sterilization of heart valve tissue using the present method results in an unexpected increase in calcification resistance which should be quite important commercially.

Although the invention has been described with regard to certain preferred embodiments which constitute the best mode presently known by the inventors for carrying out the invention, it should be understood that changes and modifications that would be obvious to one having the ordinary skill in this art may be made without departing from the scope of the invention which is set forth in the claims appended hereto. For example, although the invention has been described with regard to the sterilization of porcine aortic valves and the like, it may also be used to sterilize polymeric or metal heart valve components or other components for implantation within the human body. Although the use of an alkanol, such as isopropanol, is preferred, other organic solvents that are not deleterious to the material being sterilized may alternatively be used, e.g. toluene, and are considered to be equivalents.

Particular features of the invention are set forth in the claims which follow.

What is claimed is:

1. A process for sterilization of material by effectively killing microorganisms carried by such material, which process comprises treating such material for an effective length of time with an aqueous solution containing an effective amount of a coupling agent capable of creating amide bonds and an effective amount of an alkanol which achieves penetration of said coupling agent into the cells of microorganisms, in the optional presence of (a) a coupling enhancer that enhances the amide-creating action of said coupling agent so as to increase the number of amide bonds that are created.

2. The process for sterilization according to claim 1 wherein said alkanol is a $C_2$ to $C_4$ alkanol and is included in an amount of at least about 10 volume % of solution.

3. The process for sterilization according to claim 1 wherein said treatment is carried out at a temperature of out 25° to about 55° C.

4. The process for sterilization according to claim 1 wherein said treatment is carried out at a temperature of out 35° to about 45° C.

5. The process for sterilization according to claim 1 wherein said treatment is carried out for at least about 1 hour.

6. The process for sterilization according to claim 1 wherein said treatment is carried out for at least about 5 hours.

7. The process for sterilization according to claim 1 wherein said coupling agent is present in said solution a concentration of at least about 5 mM.

8. The process for sterilization according to claim 1 wherein said coupling agent is present in said solution a concentration of at least about 20 mM.

9. The process for sterilization according to claim 1 wherein said coupling agent is a water-soluble carbodiimide.

10. The process for sterilization according to claim 1 wherein said coupling agent is EDC.

11. The process for sterilization according to claim 10 wherein EDC is present at a concentration of at least about 20 millimolar.

12. The process for sterilization according to claim 11 wherein said solution contains at least about 1 mM sulfo-NHS as a coupling enhancer.

13. The process for sterilization according to claim 11 wherein said solution contains at least about 1 mM NHS as a coupling enhancer.

14. The process for sterilization according to claim 10 wherein said aqueous solution contains at least about 10 grams of isopropanol per 100 ml of solution.

15. The process for sterilization according to claim 1 wherein said solution contains at least about 20 grams of isopropanol per 100 ml of solution and said treatment is carried out at a temperature of between about 35° and about 45° C.

16. A process for sterilization of material by effectively killing bacteria and spores carried by such material, which process comprises treating such material for at least about 1 hour with an aqueous solution containing an effective amount of a water-soluble carbodiimide coupling agent capable of creating amide bonds, which solution contains at least about 10 volume % of a lower alkanol.

17. The process for sterilization according to claim 16 wherein said solution contains at least about 1 mM of a water-soluble coupling enhancer that enhances the amide-creating action of said coupling agent so as to increase the number of amide bonds that are created.

18. The process for sterilization according to claim 16 wherein said solution contains at least about 20 grams of a $C_3$ alkanol per 100 ml of solution.

19. A process for sterilization of biological tissue intended for implantation by effectively killing bacteria and spores, including *Bacillus subtilis,* carried by such tissue and for increasing the resistance to calcification of such tissue, which process comprises treating such tissue for at least about 1 hour at about 35° C. or higher with an aqueous solution containing at least about 25 mM of a water-soluble carbodiimide coupling agent capable of creating amide bonds, which solution contains at least about 20 volume % of isopropanol.

* * * * *

UNITED STATES PATENT AND TRADEMARK OFFICE
CERTIFICATE OF CORRECTION

PATENT NO : 5,911,951
DATED : June 15, 1999
INVENTOR(S): Girardot, et al.

It is certified that error appears in the above-identified patent and that said Letters Patent is hereby corrected as shown below:

IN THE CLAIMS:

Column 11, line 53 (claim 3), "out" should read --about--.
Column 11, line 56 (claim 4), "out" should read --about--.
Column 12, line 5 (claim 7), after "solution", insert --at--.
Column 12, line 8 (claim 8), after "solution", insert --at--.

Signed and Sealed this

Sixteenth Day of May, 2000

Attest:

Q. TODD DICKINSON

*Attesting Officer*  *Director of Patents and Trademarks*